(12) United States Patent
Signorino

(10) Patent No.: US 8,591,920 B2
(45) Date of Patent: Nov. 26, 2013

(54) STABLE LIPOPHILIC EMULSIONS FOR ACRYLIC COATING AND METHOD OF MAKING

(75) Inventor: Charles Signorino, Norristown, PA (US)

(73) Assignee: Emerson Resources, Inc., Norristown, PA (US)

( * ) Notice: Subject to any disclaimer, the term of this patent is extended or adjusted under 35 U.S.C. 154(b) by 58 days.

(21) Appl. No.: 11/163,735

(22) Filed: Oct. 28, 2005

(65) Prior Publication Data

US 2006/0057167 A1    Mar. 16, 2006

Related U.S. Application Data

(63) Continuation of application No. 10/679,101, filed on Oct. 3, 2003, now abandoned.

(51) Int. Cl.
*A61K 9/00* (2006.01)
*A61K 9/127* (2006.01)
*A61K 9/66* (2006.01)
*A61K 9/54* (2006.01)
*A61K 9/58* (2006.01)
*A61K 9/48* (2006.01)
*A61K 9/20* (2006.01)

(52) U.S. Cl.
USPC ........... 424/400; 424/450; 424/455; 424/458; 424/462; 424/463; 424/464

(58) Field of Classification Search
USPC ......... 424/400, 464, 474, 475, 482, 483, 489, 424/490, 501, 422; 514/937, 938
See application file for complete search history.

(56) References Cited

U.S. PATENT DOCUMENTS

| | | | | |
|---|---|---|---|---|
| 3,955,997 A | * | 5/1976 | Sagane et al. | 524/24 |
| 4,018,918 A | * | 4/1977 | Ayer et al. | 514/24 |
| 4,073,943 A | * | 2/1978 | Wretlind et al. | 514/772 |
| 4,436,738 A | * | 3/1984 | Bequette et al. | 514/182 |
| 4,996,193 A | * | 2/1991 | Hewitt et al. | 514/11 |
| 5,583,105 A | * | 12/1996 | Kovacs et al. | 514/11 |
| 5,952,004 A | * | 9/1999 | Rudnic et al. | 424/455 |
| 6,245,349 B1 | * | 6/2001 | Yiv et al. | 424/450 |
| 6,303,662 B1 | * | 10/2001 | Nagahama et al. | 424/522 |
| 6,451,325 B1 | * | 9/2002 | Van Nest et al. | 424/283.1 |
| 6,544,530 B1 | * | 4/2003 | Friedman | 424/400 |
| 2004/0037883 A1 | * | 2/2004 | Zhou et al. | 424/471 |

FOREIGN PATENT DOCUMENTS

| | | | |
|---|---|---|---|
| EP | 706764 A1 | * | 4/1996 |
| WO | 9840051 | * | 9/1998 |
| WO | WO9929300 | * | 6/1999 |
| WO | WO 03105606 A1 | * | 12/2003 |

OTHER PUBLICATIONS

Petereit et al, (Eur. J. Pharm. Biopharm, 1995).*
"Enteric-coated dry emulsion formulation for oral insulin delivery" by Toorisaka et al. Journal of controlled release: 107 (2005) 91-96.*

* cited by examiner

*Primary Examiner* — Isis Ghali
(74) *Attorney, Agent, or Firm* — William D. Hare; McNeely, Hare & War LLP

(57) ABSTRACT

Emulsions of lipophiles such as glycerol monostearate which are compatible with acrylic copolymer emulsions are made stable by using an emulsion stabilizer such as polysorbate 80 in an amount by weight between 1% and 5% of the lipophile and homogenizing the emulsion wherein the emulsion micelles are less than 50 microns. The ability to make a stable emulsion of a lipophile is important in the coating process as it enables preparation and shipment of the lipophilic emulsion to the coater rather than the preparation of a lipophilic emulsion at the time of the coating process which involves a heating and cooling process.

18 Claims, No Drawings

STABLE LIPOPHILIC EMULSIONS FOR ACRYLIC COATING AND METHOD OF MAKING

REFERENCE TO RELATED APPLICATIONS

This application is a continuation of U.S. patent application Ser. No. 10/679,101, filed Oct. 3, 2003, and is hereby incorporated by reference.

BACKGROUND OF THE INVENTION

The present invention relates to stable lipophilic emulsions. More particularly, the present invention relates to stable lipophilic emulsions which may be stored and shipped for use with polymers comprised of acrylic and methacrylic acid, their alkyl esters and their alkyl amino alkyl esters for the coating of pharmaceutical dosage forms.

In the past, the coating of pharmaceutical dosage forms utilizing acrylic and methacrylic acid, their alkyl esters and their alkyl amino alkyl esters usually required the addition of talc to prevent the coating from being sticky and causing defects by tablets sticking to each other or the coating equipment. The sticking together of tablets and their separation causes deformities in the coating which are referred to in the art as "picks" when the pharmaceutical dosage forms such as tablets or capsules are separated.

More recently, in U.S. Pat. No. 5,292,522—Petereit et al. describe the usefulness of a lipophilic material to replace talc in the coating composition. Petereit et al. elaborate on this coating process in Petereit et al., "Glycerol Monostearate as a Glidant in Aqueous Film-Coating Formulations", European Journal of Pharmaceutics and Biopharmaceutics, Volume 41, No. 4, pages 219-228 (1995). However, the coating method utilizing glycerol monostearate is difficult to practice due to the difficulty in preparing the lipophilic material for incorporation into the polymer emulsion. All of the examples disclosed by Petereit et al. disclose the preparation of a low solids emulsion of the lipophile, such as glycerol monostearate at 2%, at the time of coating. Also, preparation of the most useful dispersions use an emulsion stabilizer at about 40% of the lipophile. The emulsion stabilizer, a surface active ingredient, at this level may have an adverse effect on the permeability of the film. Further, since the lipophilic emulsion is not stable for periods more than several hours, the lipophilic emulsion must be prepared as a part of the process of coating the pharmaceutical dosage forms and this preparation requires heating of the ingredients, dispersing the ingredients and then cooling the dispersion before incorporation into the coating suspension. This is a cumbersome preparation process at the manufacturing and coating facility and this process of preparing the lipophilic emulsion during the coating process creates difficulties which manufacturers would like to avoid.

SUMMARY OF THE INVENTION

In accordance with the present invention, a lipophilic emulsion may be prepared at a high concentration and stabilized such that it may be stored and shipped and may be presented for use in the coating suspension at the time of coating with no heating, homogenizing or cooling.

In accordance with the present invention, a lipophile, such as glycerol monostearate, may be dispersed in water at high concentration and stabilized.

In accordance with the present invention, any quantity of lipophile may be delivered from a stable emulsion concentrate to facilitate coating suspension preparation.

In accordance with the present invention, lipophiles may be chosen from glycerol monostearate (GMS), glycerol monooleate, glycerol monolaurate, propylene glycol monolaurate, propylene glycol monooleate, propylene glycol monostearate, sorbitan monooleate, sorbitan monostearate, other glycerides including diacetylated monoglyceride and vegetable oils such as corn or coconut oils.

In accordance with the present invention, stable lipophilic emulsions may be prepared with emulsion stabilizer by weight of between 1% and 5% of the lipophile.

In accordance with the present invention, emulsion stabilizers which may be used include polysorbate 80 (PS 80), sodium lauryl sulfate and polysorbate 60.

In accordance with the present invention, plasticizers may be included in the emulsion. The plasticizers may include triethyl citrate (TEC), triacetin (TA), glycerin, propylene glycol (PG) and polyethylene glycol (PEG 400-8000 MW).

Briefly and basically, the present invention comprises an emulsion wherein a lipophile is chosen from the group consisting of glycerol monostearate, glycerol monooleate, glycerol monolaurate, propylene glycol monolaurate, propylene glycol monooleate, propylene glycol monostearate, sorbitan monooleate, sorbitan monostearate, diacetylated monoglyceride and vegetables oils. An effective amount of an emulsion stabilizer such as polysorbate 80 is used. An effective amount of an emulsion stabilizer may be by weight between 1% and 5% of the lipophile. The lipophile and the emulsion stabilizer are homogenized to form micelles having a size of 50 microns or less. This emulsion is stable for a period of at least three months.

Briefly, in accordance with the method of the present invention, an emulsion of a water insoluble lipophile is produced by bringing the water to a temperature of between 60 and 80 degrees centigrade, adding the lipophile, adding an emulsion stabilizer, stirring vigorously for approximately 5 minutes, passing the mixture through a homogenizer for between about 10 to 120 minutes and cooling the emulsion to room temperature while stirring. The 10 to 120 minutes corresponds to 3 to 10 passes of the formulation through a homogenizer or, in other words, 3 to 10 cycles.

DETAILED DESCRIPTION OF THE PREFERRED EMBODIMENTS

In accordance with the present invention, a lipophile such as glycerol monostearate, can be dispersed in water at high concentrations to prepare stable emulsions that can be stored and shipped for later use with emulsions of polymers comprising acrylic acid and methacrylic acid, their alkyl esters and their alkyl amino alkyl esters for coating pharmaceutical dosage forms without having to prepare a lipophilic emulsion at the coating location.

Lipophiles that may be utilized in practicing the invention include, in addition to glycerol monostearate, glycerol monooleate, glycerol monolaurate, propylene glycol monolaurate, propylene glycol monooleate, propylene glycol monostearate, sorbitan monooleate, sorbitan monostearate, as well as other glycerides such as diacetylated monoglyceride (i.e. Myvacet 9-45, commercially available from Quest International, 5115 Sedge Boulevard, Hoffman Estates, Ill., 60192), and vegetable oils such as corn and coconut oils. The stable lipophilic emulsions may be used directly with the acrylic polymers without any heating, homogenizing or cooling to form the lipophilic emulsion. Any quantity of lipophile may be delivered from a stable lipophilic emulsion concentrate to facilitate coating suspension preparation.

In accordance with the present invention, stable dispersions or emulsions of the various lipophiles may be prepared with an emulsion stabilizer such as polysorbate 80 using only an amount of the emulsion stabilizer which is 1% to 5% of the weight of the lipophile. Other emulsion stabilizers may be used including sodium lauryl sulfate and polysorbate 60.

In accordance with the present invention, the lipophilic emulsion remains stable with the use of plasticizers in the suspension. The plasticizers may include triethyl citrate (TEC), triacetin (TA), glycerin, propylene glycol (PG) and polyethylene glycol (PEG 400-8000 MW). These dispersions can be added to all of the acrylic resin copolymer dispersions. Some acrylic copolymers are available as dry 100% powders, for example, Eudragit L100, commercially available from Rohm America LLC, 2 Turner Place, Piscataway, N.J. 08855. Such acrylic copolymers need to be dispersed into water before adding the lipophilic emulsion to produce the coating composition.

The following is an example of a lipophilic emulsion in accordance with the present invention.

EXAMPLE 1

| Material | Quantity |
| --- | --- |
| Glycerol Monostearate (GMS) | 10.00 kg |
| Triethyl Citrate (TEC) | 9.60 (20.00% solids) |
| Polysorbate 80 (PS80) | 0.40 |
| Water | 80.00 |

In preparing the lipophilic emulsion of Example 1, water was charged to a 50 gallon tank and heated to 70 degrees centigrade with stirring. The triethyl citrate and polysorbate 80 were added and the temperature was raised to 70 degrees centigrade. The glycerol monostearate was sprinkled onto the surface of the water slowly allowing it to melt and to be incorporated into the suspension. The mixture was stirred vigorously with a propeller mixer. The mixture was passed through an in-line homogenizer for 15 minutes, recirculating into the stirred batch. The suspension was inspected under a microscope at 100 magnification and the emulsion contained micelles of about 10 microns. The homogenizer was turned off and the batch was cooled with stirring to 30 degrees centigrade.

The homogenizer utilized in preparing Example 1 was manufactured by Silverson Machines, Inc., 355 Chestnut Street, East Longmeadow, Mass. 01028. The mixture should be passed through the in-line homogenizer for 3 to 10 cycles and it is believed that it is important to produce micelles of 50 microns or less in order to produce the stability of the emulsion desired by the invention. The 3 to 10 cycles would take from 10 to 120 minutes. The emulsion produced is stable for at least three months and this allows adequate time for packaging, storage and distribution to manufacturers and use by the manufacturer in the coating process.

Preservatives may be added and the lipophilic emulsion may be packaged for storage and distribution to manufacturers in the pharmaceutical industry for use in connection with acrylic coating processes. The emulsion may be shipped concentrated and effectively diluted by the coater at the time of coating.

The lipophilic emulsion of Example 1 may be used in various acrylic resin copolymer coatings, a specific example is illustrated in Example 2.

EXAMPLE 2

| Material | Quantity |
| --- | --- |
| USP/NF methacrylic acid copolymer (30%) | 60 parts |
| Lipophilic emulsion of Example 1 | 10 (20% solids) |
| Water | 30 |

The methacrylic acid copolymer emulsion (i.e. Eudragit L30D55 commercially available from Rohm America LLC) and water were added to a container and stirred at room temperature. The lipophilic emulsion of Example 1 was added with stirring and stirred for one hour. This enteric coating suspension was ready for spraying in a fluid bed coater or side vented coating machine. This is a very desirable, simplified procedure for making a coating suspension using acrylic copolymers with a pre-emulsified lipophile. The coating suspension may be colored if desired by stirring in a dispersion of any of the FD&C, D&C or uncertified colorants approved for use in the pharmaceutical industry. Uncertified colorants include titanium dioxide, iron oxides, other minerals and natural colors.

Additional examples of stable lipophilic emulsions are as follows.

EXAMPLE 3

| Material | Quantity |
| --- | --- |
| GMS | 15.0 kg |
| TEC | 9.8 (25% solids) |
| PS80 | 0.2 |
| Water | 75.0 |

EXAMPLE 4

| Material | Quantity |
| --- | --- |
| GMS | 19.8 |
| PS80 | 0.2 (20% solids) |
| Water | 80 |

EXAMPLE 5

| Material | Quantity |
| --- | --- |
| Glycerol Monooleate | 10.0 |
| TEC | 9.8 |
| PS80 | 0.2 (20% solids) |
| Water | 80 |

EXAMPLE 6

| Material | Quantity |
| --- | --- |
| Sorbitan Monostearate | 10.0 |
| PEG 400 | 9.8 |
| PS80 | 0.2 (20% solids) |
| Water | 80 |

EXAMPLE 7

| Material | Quantity |
| --- | --- |
| GMS | 10.0 |
| TEC | 9.9 |
| PS80 | 0.1 (20% solids) |
| Water | 80 |

In accordance with the present invention, a wide variety of lipophilic materials may be emulsified for inclusion into acrylic coating emulsions.

Another example of the use of a lipophilic emulsion in an acrylic coating emulsion is shown in Example 8.

EXAMPLE 8

| Material | Quantity |
| --- | --- |
| Ammonium methacrylate copolymer (30%) | 60.0 |
| Lipophilic emulsion of Example 7 | 6.0 (21.2% solids) |
| TEC 2.0 | 2.0 |
| Water | 32.0 |

This blend may be stirred for an hour and sprayed on tablets, capsules or granules in side vented pans or fluid bed columns.

The present invention may be embodied in other specific forms without departing from the spirit or essential attributes thereof and, accordingly, reference should be made to the appended claims, rather than to the foregoing specification as indicating the scope of the invention.

What is claimed is:

1. A liquid emulsion, consisting essentially of:
a lipophilic phase comprising one or more lipophiles;
a water phase, wherein when the water phase comprises ingredients in addition to the water in the water phase, the ingredients are present in an amount less than the amount of the water present in the water phase;
the lipophile selected from the group consisting of glycerol monostearate, glycerol monooleate, glycerol monolaurate, propylene glycol monolaurate, propylene glycol monooleate, propylene glycol monostearate, sorbitanmonooleate, sorbitanmonostearate, diacetylatedmonoglyceride and vegetable oils;
an effective amount of an emulsion stabilizer between 1% and 5% of the lipophile and said emulsion stabilizer is selected from the group consisting of polysorbate 80 and polysorbate 60; and
a plasticizer;
wherein said lipophile, plasticizer, and emulsion stabilizer are homogenized in water to form micelles having an average particle size of about 10 microns to about 50 microns, and wherein the lipophile remains emulsified in the liquid emulsion for at least 3 months.

2. An emulsion in accordance with claim 1 wherein the plasticizer is selected from the group consisting of triethyl citrate, triacetin, glycerin, propylene glycol and polyethylene glycol.

3. An emulsion in accordance with claim 2 wherein said emulsion is compatible with an emulsion of copolymers of acrylic and methacrylic acids and their alkyl esters and alkyl amino alkyl esters.

4. An emulsion in accordance with claim 1 wherein said emulsion stabilizer is polysorbate 80 at about 0.2% and a lipophile is glycerol monostearate at about 10% and wherein triethyl citrate at about 9.8% is used as a plasticizer, the remainder being water.

5. An emulsion in accordance with claim 1 wherein said effective amount of an emulsion stabilizer is by weight about 2% of the lipophile.

6. An emulsion in accordance with claim 1 wherein said emulsion stabilizer is polysorbate 80 at about 0.2% and the lipophile is glycerol monooleate about 19.8%.

7. An emulsion in accordance with claim 1 wherein said emulsion stabilizer is polysorbate 80 at about 0.3% and the lipophile is glycerol monostearate at about 10% and wherein said plasticizer is triethyl citrate at about 9.7%.

8. An emulsion in accordance with claim 1 wherein said emulsion stabilizer is polysorbate 80 at about 0.1% and the lipophile is glycerol monostearate at about 10% and wherein said plasticizer is triethyl citrate at about 9.9%.

9. An emulsion in accordance with claim 1 wherein the emulsion stabilizer is polysorbate 80 at about 0.2% and the lipophile is glycerol monostearate at about 10%, and wherein the plasticizer is polyethylene glycol 8000 at about 9.8%.

10. An emulsion in accordance with claim 1 wherein the lipophile is 5% to 20% by weight.

11. An emulsion in accordance with claim 2 wherein the plasticizer is up to 20% of the formulation.

12. An emulsion in accordance with claim 1 wherein the emulsion stabilizer is about 0.1% to 2% of the formulation.

13. An emulsion in accordance with claim 1 which is adaptable to be stirred into an acrylic copolymer emulsion to form a stable coating suspension with a lipophile to resin ratio of between 1:10 and 1:50 for coating in side vented pans and fluid bed columns onto powders, granules, tablets or capsules.

14. An emulsion in accordance with claim 1 which is adapted to be stirred into an acrylic copolymer emulsion containing colorants at 10% to 50% of the resin content of the formulation.

15. An emulsion of a water insoluble lipophile produced by:
providing water for a water phase of the emulsion;
heating the water to a temperature of between 60 and 80 degrees centigrade;
adding one or more lipophiles to the water while stirring, the one or more lipophiles selected from the group consisting of glycerol monostearate, glycerol monooleate, glycerol monolaurate, propylene glycol monolaurate, propylene glycol monooleate, propylene glycol monostearate, sorbitanmonooleate, sorbitanmonostearate, diacetylatedmonoglyceride and vegetable oils;
adding an effective amount of an emulsion stabilizer, the emulsion stabilizer being present at between 1% and 5% of the one or more lipophiles, wherein said emulsion stabilizer is selected from the group consisting of polysorbate 80 and polysorbate 60;
adding a plasticizer;
stirring vigorously for approximately five minutes to form a mixture;
passing the mixture through a homogenizer for between about 10 to about 120 minutes to form micelles;
cooling the emulsion to room temperature while stirring;
wherein the lipophile remains emulsified in the liquid emulsion for a period of at least three months and the micelles have an average particle size of about 10 microns to about 50 microns,
wherein the emulsion consists essentially of the water phase, the one or more lipophiles, the emulsion stabilizer and the plasticizer, wherein when the water phase comprises ingredients in addition to the water in the water phase, the ingredients are present in an amount less than the amount of the water present in the water phase.

16. A method in accordance with claim 15 wherein said step of passing the mixture through a homogenizer for between about 10 to about 120 minutes comprises passing the mixture through the homogenizer for between 3 and 10 cycles.

17. A method in accordance with claim 15 wherein said step of passing the mixture through a homogenizer for between about 10 to about 120 minutes is carried out to produce micelles of less than 50 microns.

18. A sprayable liquid suspension of polymers and the liquid emulsion of claim 1.

* * * * *